United States Patent [19]

Bernard et al.

[11] Patent Number: 4,697,598
[45] Date of Patent: Oct. 6, 1987

[54] EVOKED POTENTIAL AUTOREFRACTOMETRY SYSTEM

[75] Inventors: Thomas E. Bernard, Whitehall; Emile M Roth, Pittsburgh; Edwin R. Mohan, Braddock Hills; Gary W. Sherwin, South Huntingdon Township, Westmoreland County; John M. Zomp, N, Huntingdon, all of Pa.

[73] Assignee: Westinghouse Electric Corp., Pittsburgh, Pa.

[21] Appl. No.: 727,032

[22] Filed: Apr. 25, 1985

[51] Int. Cl.⁴ .......................... A61B 3/10; A61B 5/04
[52] U.S. Cl. .................................. 128/731; 128/745; 128/642; 128/644; 351/205
[58] Field of Search .............................. 128/639-644, 128/731-732, 745, 802-803; 351/205, 216-217, 220

[56] References Cited

U.S. PATENT DOCUMENTS

| | | | |
|---|---|---|---|
| 3,111,478 | 11/1963 | Watanabe | 204/416 |
| 3,421,498 | 1/1969 | Gans | 128/731 |
| 3,508,541 | 4/1970 | Westbrook et al. | 128/644 |
| 3,620,208 | 11/1971 | Higley et al. | 128/639 X |
| 3,663,098 | 5/1972 | Merchant | 351/216 X |
| 3,804,080 | 4/1974 | Ruttgers et al. | 128/642 |
| 3,893,450 | 7/1975 | Ertl | 128/731 |
| 3,998,213 | 12/1976 | Price | 128/644 |
| 4,085,739 | 4/1978 | Sams | 337/404 |
| 4,181,407 | 1/1980 | Razran | 351/205 |
| 4,304,242 | 12/1981 | Siarkiewicz et al. | 128/745 |
| 4,323,076 | 4/1982 | Sams | 128/644 |
| 4,417,592 | 11/1983 | John | 128/731 |
| 4,442,315 | 4/1984 | Segawa | 128/639 X |
| 4,464,412 | 8/1984 | Washburn | 128/803 X |
| 4,493,539 | 1/1985 | Cannon, Jr. | 351/205 |
| 4,501,276 | 2/1985 | Lombardi | 128/642 |
| 4,528,989 | 7/1985 | Weinblatt | 128/745 |

FOREIGN PATENT DOCUMENTS

| | | | |
|---|---|---|---|
| 3331799 | 3/1984 | Fed. Rep. of Germany | 351/217 |
| 2026752 | 2/1980 | United Kingdom | 128/745 |

OTHER PUBLICATIONS

"Rapid Objective Refraction Using Evoked Brain Potentials", D. Regan, *Investigative Opthalmology*, Sep. 1971, pp. 669-679.

"Rapid Assessment of Visual Function: an Electronic Sweep Technique for the Pattern Visual Evoked Potential", Christopher W. Tyler et al., *Invest. Opthalmol. Visual Sci.*, Jul. 1979, pp. 703-713.

"Evoked Potential Correlates of Display Image Quality", Frank E. Comer et al., *Human Factors*, 1978, pp. 589-596.

"Recent Advances in Electrical Recording from the Human Brain", D. Regan, *Nature*, vol. 253, Feb. 6, 1975, pp. 401-407.

(List continued on next page.)

*Primary Examiner*—Kyle L. Howell
*Assistant Examiner*—Angela D. Sykes
*Attorney, Agent, or Firm*—Daniel C. Abeles

[57] ABSTRACT

An evoked potential autorefractometry system includes a computer driving an alternating checkerboard mirror stimulus to project a stimulus pattern directly to a patient through a continuously variable focus lens controlled by the computer and which maintains a constant image size on the patient's retina. The evoked potentials produced by the patient are amplified, asychronously filtered both in an analog and digital fashion to allow peak to peak detection of the evoked potentials to determine amplitude. The digital filter includes a 255 point running sum. The peak to peak amplitudes are asychronously digitally filtered using a 16 point running sum to produce an amplitude measure of the evoked potentials. The lens is swept rapidly from one extreme of focus to the other extreme in relatively large steps to determine the area in which the peak amplitude occurs. The lens is then subsequently swept in smaller and smaller range sweeps using smaller and smaller steps around the peak amplitude until the peak in the amplitude is pinpointed within a desired diopter at which point the lens position is printed out on the printer as the patient's prescription.

41 Claims, 17 Drawing Figures

OTHER PUBLICATIONS

"Watching the Brain at Work", *IEEE Spectrum*, Mar. 1983, pp. 52–57.

"Microcomputer-Controlled Visual Stimulator for Studies of Eye Movements and Vep's"; *Med and Biol. Eng. and Comput.*, 1979, pp. 781–782.

Spraker et al.; "Electronic Checkerboard Pattern Generator for Vision Research"; Electroencephalography and Cun. Neurophys., vol. 42, No. 2, 2-1977, pp. 259–263.

Dymek et al.; "Goggle System Using Electrically Activated Liquid Crystal Shutters for Use in Vep Tests"; *Proc. of 7th NE Bioeng. Conf.*, 11-1979, pp. 45–48.

Sokol et al., "Visual Evoked Potentials", (article).

Regan, "Electrical Responses Evoked from the Human Brain", *Scientific America*, 1979, pp. 134–146.

Regan, "Evoked Potential Indications of Color Blindness", *Vision Res.*, vol. 14, 1973, pp. 89–95.

Cannon, "Contrast Sensitivity: Psychophysical and Evoked Potential Methods Compared", Vison Res., vol. 23, 1983, pp. 87–95.

EVOKED POTENTIAL AUTOREFRACTOMETRY SYSTEM

CROSS-REFERENCES TO RELATED APPLICATIONS

This application is related to the following concurrently filed copending U.S. patent applications assigned to the assignee of the present invention: Electroencephalographic (EEG) Cap by Sherwin having U.S. Ser. No. 727,031; Low Noise EEG Probe Wiring System by Sherwin having U.S. Ser. No. 727,060, now allowed Subcaratinaceous EEG Probe by Sherwin and Mohan having U.S. Ser. No. 727,033, U.S. Pat. No. 4,632,120; Shielded, Self-Preparing Electrode Suitable for EEG Mapping by Sherwin having U.S. Ser. No. 727,058, U.S. Pat. No. 4,640,290; Narrow Band EEG Amplifier by Sherwin and Zomp having U.S. Ser. No. 727,056, now allowed; and Phase Lock Stepper Motor Controlled Light Chopper by Sherwin U.S. Ser. No. 727,156 U.S. Pat. Nos. 4,631,466, 52,438.

BACKGROUND OF THE INVENTION

1. Field of the Invention

The present invention relates to an autorefractometry system suitable for prescribing eyeglass or contact lenses and, more particularly, to an evoked potential autorefractometry system which uses a steady state evoked potential and which is low in cost, does not intimidate patients and provides a highly accurate refractive lens prescription.

2. Description of the Related Art

FIG. 1 illustrates a refractometer typically found in an eye doctor's office. In such a refractometer, lenses of differing refractive power are placed in front of the patient's eyes as the patient indicates whether or not the visual target has improved in focus. Such a system for prescribing eye glass lenses is subjective, requires verbal cooperation from the subject, is not suitable for communication handicapped persons and is very time consuming.

Fig. 1B illustrates a prior art acuity testing system. This movable lens system for generating steady state evoked potential amplitudes has been proposed by Regan in "Rapid Objective Refraction Using Evoked Brain Potentials", *Investigative Opthamology*, Vol. 12, No. 9, September 1973. In the Regan system, a light projector 20 projects light through a vibrating bar or check transparency 21, through a movable projection focus lens 22 onto a reflecting screen 23 which reflects the alternating stimulus back to the patient 24 through cylindrical lens 28. The evoked potentials are amplified by EEG amplifier 25 and applied to a filtering unit 26 which drives an XY plotter 27. The filter 26 is a synchronous filter that uses the properties of the pythagorean theorem to filter the input signal and produce an amplitude of the evoked potentials. Regan suggested that a digital Fourier transform could be substituted for the filter 26. A cathode ray tube or television has been suggested by Gomer in "Evoked Potential Correlates of Display Image Quality", *Human Factors*, October 1978, as suitable for an evoked potential stimulus source. Tyler et al in "Rapid Assessment of Visual Function: An Electronic Sweep Technique for the Pattern Visual Evoked Potential" uses a synchronous filter and integrator as a substitute for Regan's filter unit 26 and also used a sine wave grating with a reversal rate of 24 hertz to produce an XY plot of evoked potential amplitude versus spatial frequency for each discrete lens. Such a synchronous filter system requires at least 20 seconds for each sweep of each lens as acuity is being determined.

SUMMARY OF THE INVENTION

It is an object of the present invention to provide an evoked potential autorefractometry system suitable for a commercial environment.

It is another object of the present invention to provide a simple, low cost stimulus source in an evoked potential autorefractometry system.

It is a further object of the present invention to provide an evoked potential refractometry system small in size and low in cost that does not require an expensive Fourier Transform unit or synchronous filter.

It is another object of the present invention to provide a system that does not need a cumbersome image screen.

It is an additional object of the present invention to provide a low noise, high reliability shielded visual testing system suitable for a commercial environment.

It is yet another object of the present invention to provide an evoked potential autorefractometry system that does not intimidate the patient.

It is still a further object of the present invention to provide a vision testing system that does not rely on the subjectivity of the subject, but provides an objective measure of a lens which provides the sharpest presentation of a visual object to a patient.

It is another object of the present invention to provide a system that tests vision rapidly and accurately.

The above objects are accomplished by an evoked potential autorefractometry system that includes a computer-driving an alternating checkerboard mirror stimulus to stimulate a patient through a continuously variable focus zoom type lens that is controlled by the computer and maintains a constant image size on the patient's retina. The steady state evoked potentials produced by the patient are amplified, filtered both in an analog and digital fashion to allow peak to peak detection of the evoked potentials to determine amplitude. The peak to peak amplitudes are filtered to produce an average evoked potential amplitude. The lens is first swept rapidly from one extreme of focus to the other extreme in relatively large steps to determine the area in which the peak amplitude occurs. The lens is then subsequently swept in smaller and smaller range sweeps at smaller and smaller steps around the maximum amplitude until the maximum in amplitude is pinpointed at which point the lens position is printed out on the printer as the patient's diopter prescription.

These, together with other objects and advantages which will be subsequently apparent, reside in the details of construction and operation of the system as more fully hereinafter described and claimed, reference being had to the accompanying drawings forming a part hereof wherein like reference numerals refer to like parts throughout.

DESCRIPTION OF THE PREFERRED EMBODIMENTS

Figure 2:
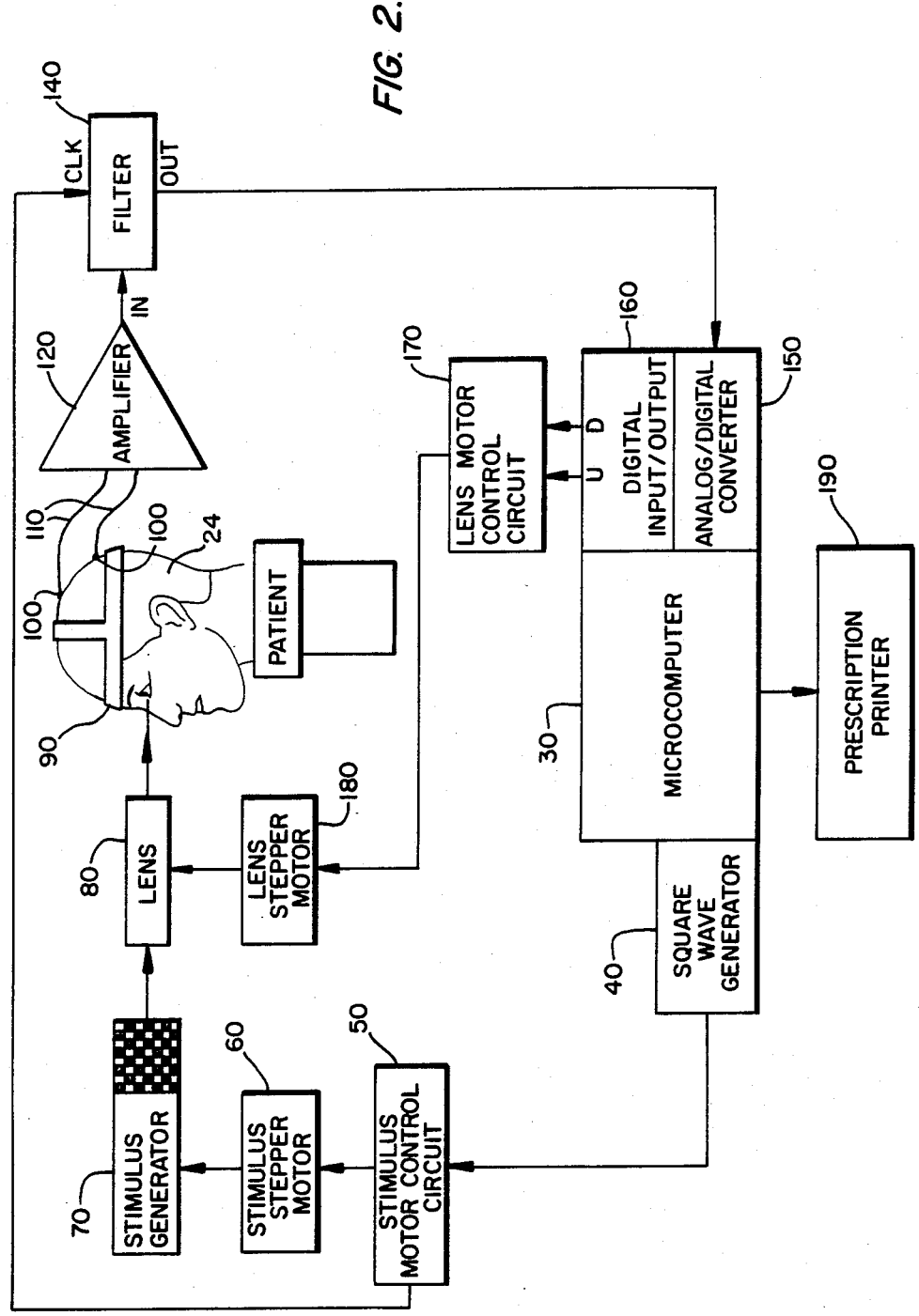
FIG. 2 is a block diagram of an evoked potential autorefractometry system according to the present invention.
Figure 3:
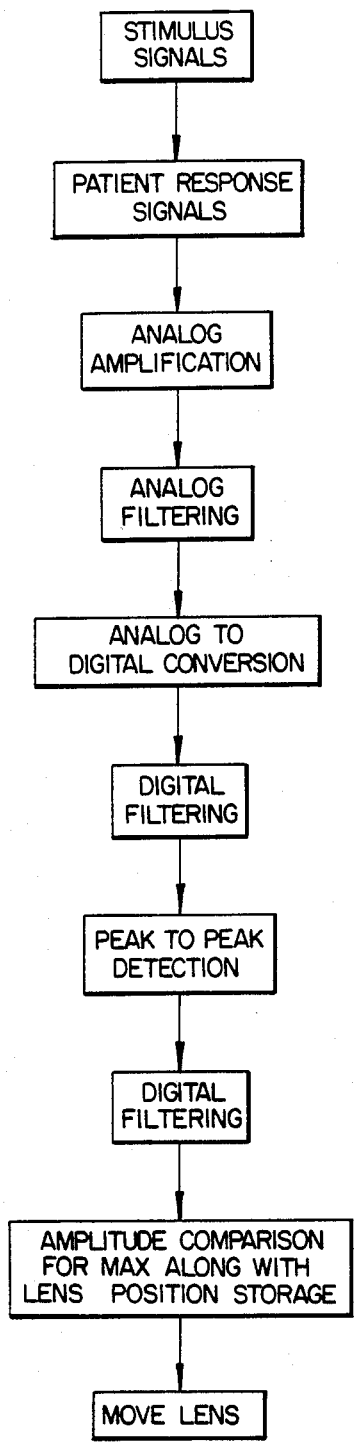
FIG. 3 is a block diagram illustrating the conceptual operation of the system of FIG. 3.

FIG. 2 illustrates in block diagram form the major components of an evoked potential autorefractometry system used to prescribe patients' lenses and print out the prescription. FIG. 3 conceptually illustrates the general operation of the present invention. With respect to both FIG. 2 and FIG. 3, microcomputer 30 activates square wave generator 40 to produce a fixed frequency square wave used by stimulus motor control circuit 50 to control stepper motor 60. The stepper motor 60 controls a checkerboard pattern stimulus generator 70 which projects an alternating checkerboard pattern through continuously variable lens 80 to the patient 24. The amplitude modulated steady state evoked potential produced by the patient includes a very strong fundamental signal at the frequency of the reversal rate of the stimulus, along with undesired harmonics, muscle movement noise and environmental noise. An EEG cap 90 including self-preparing electrodes 100 detects the evoked potentials produced by the patient in response to the alternating changing focus stimulus and transmits the evoked potentials over low noise wiring system 110 to high gain, low noise amplifier 120. The amplifier 120, after boosting the signal level of the evoked potentials, applies the evoked potentials to a very narrow bandpass filter 140 which produces a steady state evoked potential signal free from harmonics and relatively free from noise. The steady state evoked potential signal is applied to an analog-to-digital converter 150 coupled to the microcomputer 30. The microcomputer 30 performs digital filtering followed by peak to peak detection followed by digital filtering which results in average peak to peak amplitude. Essentially the system performs amplitude demodulation of a six hertz signal which was amplitude modulated by varying the focus of the lens. The average peak to peak amplitude or demodulated signal is continually compared to determine the maximum amplitude which coincides with maximum visual acuity. The microcomputer 30 stores the position of the lens 80 associated with the maximum amplitude. The microcomputer 30 also controls the lens 80 through digital input/output unit 160, lens motor control circuit 170 and stepper motor 180 to sweep the lens 80 from one extreme of focus, for example −15 diopter, to the other extreme of focus, for example +15 diopter. During the first sweep, the lens 80 should be moved in increments of 0.08 diopter to provide a relatively continuous change in focus which prevents step or impulse type responses by the eye. During subsequent sweeps, the diopter step can be reduced down to 0.02 diopter if desired. Each sweep should last approximately one minute to prevent fatigue from becoming a problem. After each sweep, the range and lens step size are reduced around the maximum amplitude which was previously detected and another sweep in the opposite direction occurs from the stopping position. The range/step size reduction and sweep process continues until the lens 80 position at which maximum amplitude occurs is determined within desired diopter limits at which point the lens 80 position is printed out by prescription printer 190 as the subject's prescription. Present eyeglass or contact lens making technology requires a precision of one-quarter diopter and the present system can easily provide a prescription within one-quarter diopter.

A microcomputer, such as a Commodore 64, is particularly suitable as the microcomputer 30 since it includes a square wave generator 40, commonly called a tone generator, which operates independently of the microcomputer 30. During initialization and start-up of the autorefractometry system, the microcomputer 30 loads into the square wave generator 40 a control word which causes the generator 40 to produce a square wave at a frequency of 2.4 kilohertz. The analog-to-digital converter 150 and digital input/output unit 160 are available as a single plug compatible board designated an MW 611 available from Micro West Electronics and purchasable from Micro World Electronix, Inc. located in Lakewood, Colorado.

Figure 4:
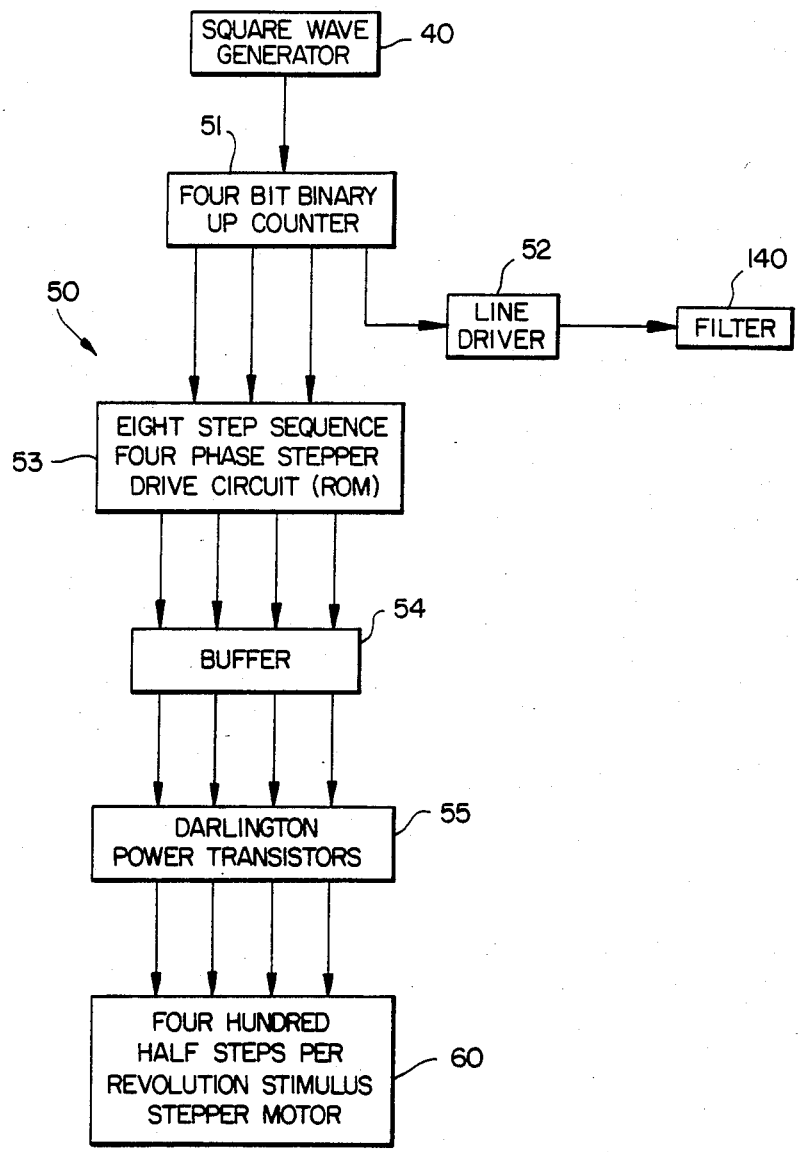
FIG. 4 is a block diagram of the stimulus motor 60 and control circuit 50 for controlling the stimulus stepper motor 60 of FIG. 2.

The 2.4 kilohertz signal generated by square wave generator 40 is applied to the stimulus motor control circuit 50 illustrated in FIG. 4 to control stepper motor 60. The 2.4 kilohertz square wave is applied to a four bit binary up counter 51 which generates a 1.2 kilohertz signal applied as a clock signal to filter 140 through line driver 52. The four bit binary up counter 51 can be a 74LS193 available from Texas Instruments. Three bits $B_1$–$B_3$ of the output of the binary counter 51 are applied to an 8-step sequence 4-phase stepper drive circuit 53 which can be a ROM designated DM87S188 manufactured by National Semiconductor. A ROM map in accordance with Table 1 below is suitable for converting the binary count into 4-drive signals for the stepper motor 60.

TABLE 1

| Input | | | Output | | | |
|---|---|---|---|---|---|---|
| $B_3$ | $B_2$ | $B_1$ | $D_3$ | $D_2$ | $D_1$ | $D_0$ |
| 0 | 0 | 0 | 1 | 1 | 0 | 1 |
| 0 | 0 | 1 | 1 | 0 | 0 | 1 |
| 0 | 1 | 0 | 1 | 0 | 1 | 1 |
| 0 | 1 | 1 | 1 | 0 | 1 | 0 |
| 1 | 0 | 0 | 1 | 1 | 1 | 0 |
| 1 | 0 | 1 | 0 | 1 | 1 | 0 |
| 1 | 1 | 0 | 0 | 1 | 1 | 1 |
| 1 | 1 | 1 | 0 | 1 | 0 | 1 |

The four position drive signals $D_1$–$D_3$ are applied to buffer 54 which can be a CD 4050 manufactured by RCA. The buffer 54 applies the drive signals to Darlington power transistors 55 Model MC1411 manufactured by Motorola which control the position of a 400 half step per revolution stimulus stepper motor 60. The stimulus stepper motor 60 can be a stepper motor manufactured by SLOSYN of Superior Electric of Bristol, Connecticut and designated Model No. M03. Additional details concerning the construction and operation of the stimulus stepper motor control circuit can be found in the concurrently filed copending application entitled "Phase Locked Stepper Motor Controlled Light Chopper" mentioned in the crossreferences section and which is incorporated herein by reference.

Figure 5:
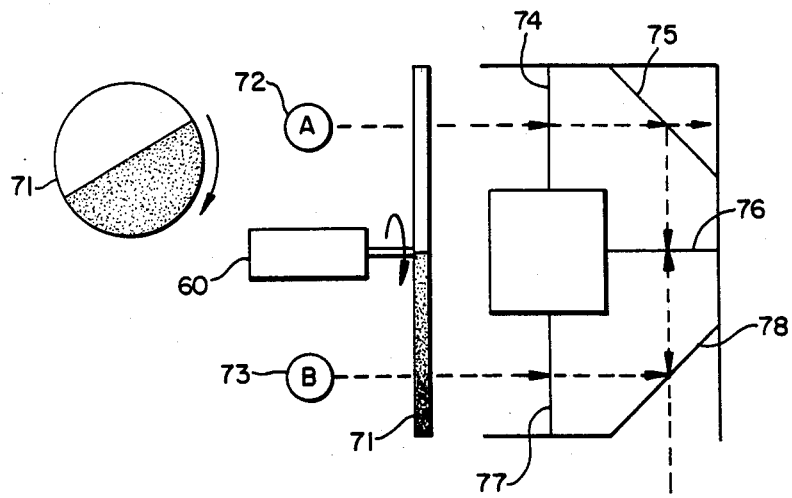
FIG. 5 is a block diagram of the checkerboard mirror stimulus generator 70 of FIG. 2.
Figure 5:
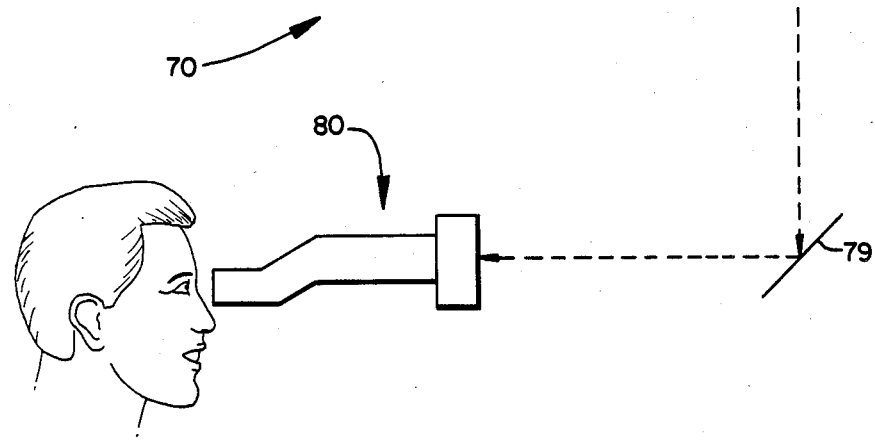

The stepper motor 60 spins a chopper wheel 71 in the stimulus generator 70 as illustrated in FIG. 5. The chopper wheel 71, spinning at three cycles per second, alternately interrupts light sources A and B designated as 72 and 73 which can be ordinary 75 watt incandescent bulbs. The three hertz chopper wheel 71 spin rate produces a pattern reversal rate of six hertz which is in the frequency range where patients produce the maximum amplitude steady state evoked potentials. The light from light source A is transmitted through matte filter 74 and reflected off beam splitter 75. Beam splitter 75 reflects the light through checkerboard mirror 76 which is positioned approximately 32 inches in light path length from the lens 80. The checkerboard mirror 76 should have a check spacial frequency of 8 cycles per inch (16 inch checks) to obtain maximum evoked potentials from the subject with the lens 80, described hereafter with respect to FIG. 6, positioned at a distance of 32 inches from the mirror 76. The checks should provide an alternating achromatic black and white pattern, which provides the largest evoked potential as compared to other colors, and should have a contrast ratio of at least 60 percent for the best evoked potential. The light from light source B transmitted through matte filter 77, is reflected off beam splitter 78. The checkerboard mirror 76 reflects the light back to beam splitter 78 which transmits the light from the front of checkerboard mirror 76 toward the patient 24. The light can optionally be reflected off of a mirror 79. The mirror 79 allows the stimulus generator and lens combination to be arranged in a more compact space. The light from light sources A 72 and B 73 must travel approximately equal length paths to the subject to maintain the proper contrast ratio, so care must be taken in producing the stimulus generator 70. In addition, a beam splitter 75 must be used which matches beam splitter 78, rather than a 100 percent mirror so that the proper contrast ratio is maintained. The various mirrors, matte filters and beam splitters are commonly available from an optical supply house.

When the alternating checkerboard stimulus pattern leaves the stimulus generator 70, it passes through lens 80 which is positioned against the eye of subject 24. Lens 80 is a continuously variable focus lens that includes a geared focus. The lens 80 must provide a constant image size to the subject's retina so that variations in stimulus pattern size on the retina do not cause variations in the amplitude of the evoked potential produced by the subject. The design of such a continuously variable focus lens 80 with a geared focus that produces a constant image size is available from Optical Research Associates of Pasadena, California at a relatively high cost.

Figure 6:
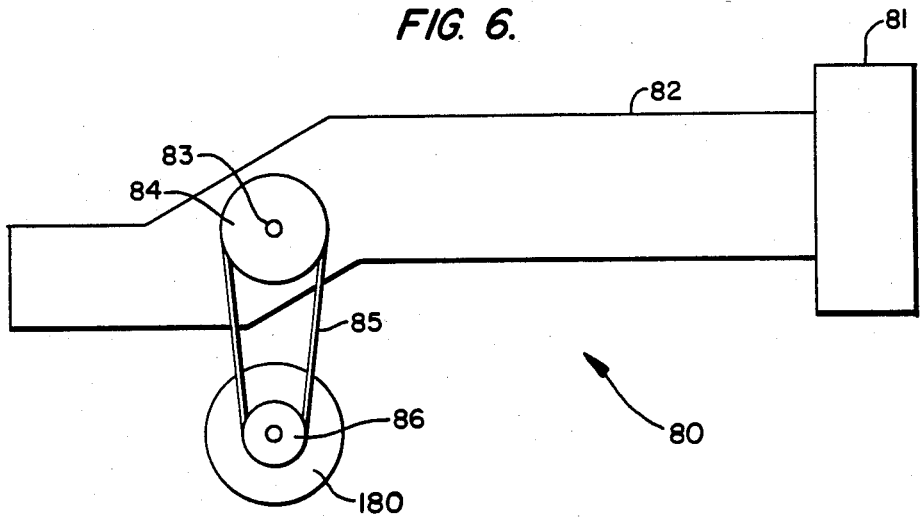
FIG. 6 is a diagram illustrating the construction of lens 80.

A more cost effective version of the lens 80 can be constructed from commercially available parts as illustrated in FIG. 6. Light from stimulus generator 70 enters a +1 diopter close-up lens 81 available from Tiffen of Hauppauge, New York. The close-up lens 81 includes a screw thread adapter which mates with a 17×60 telescope 82 available from any optical supply house. A suitable telescope 82 can be obtained from a K-Mart Department Store and is designated a Focal Telepscope having Model No. 20-20-63. The telescope 82 should have focus control rod 83 which can be fitted with a chain sprocket 84. The telescope 82 focus is adjusted through chain 85 by sprocket 86 attached to lens stepper motor 180. A step down ratio between sprockets 84 and 86 should be 1.5. A suitable chain and sprocket set is available from Boston Gear. The lens stepper motor 180 and lens stepper motor control circuit 170 are discussed later.

Figure 7:
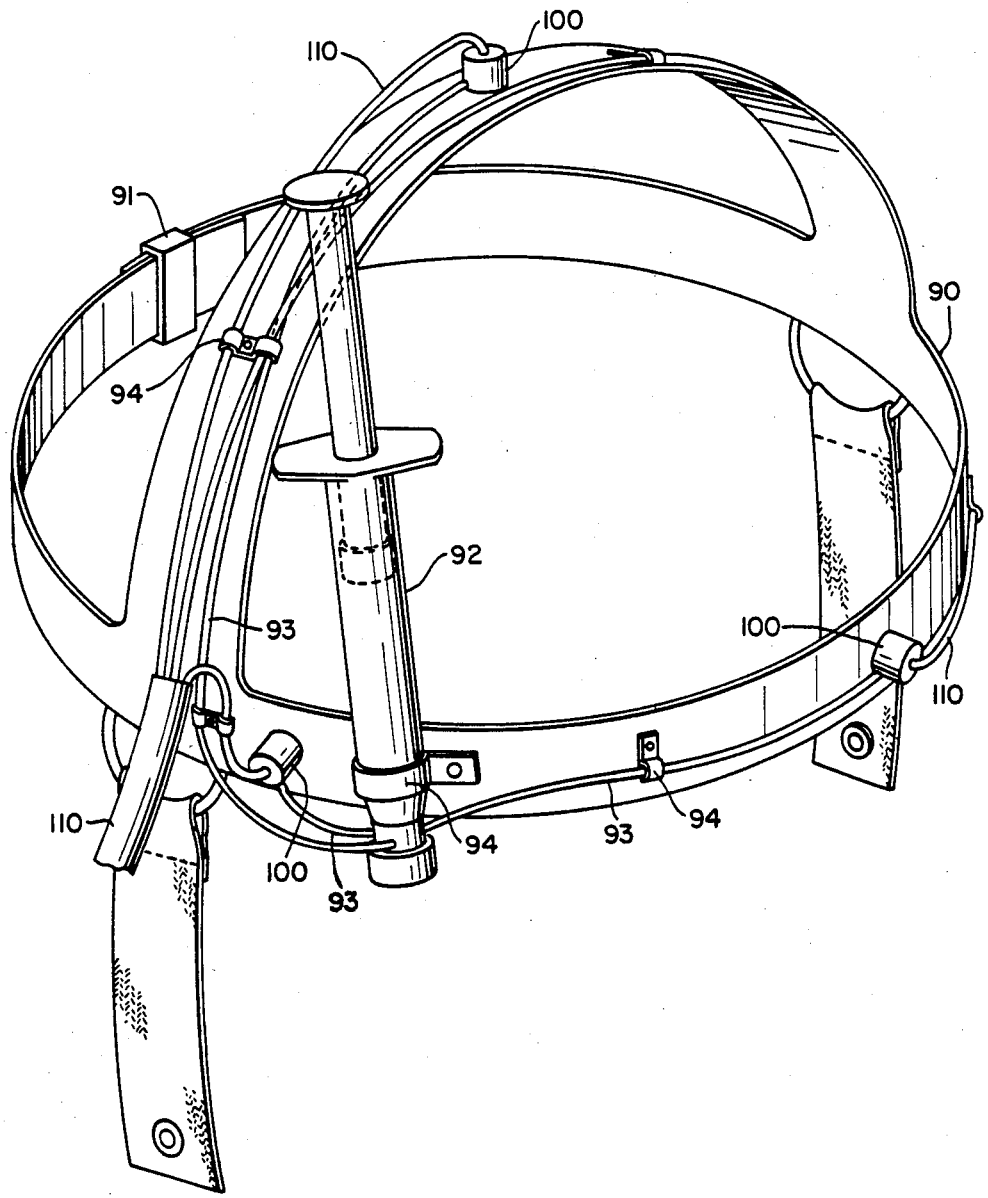
FIG. 7 is a perspective view of an EEG cap 90 including self-preparing electrodes 100 for a patient's head.

When the patient produces evoked potentials in response to the alternating stimulus, the potentials are picked up by self-preparing electrodes 100 mounted in an EEG cap 90 at positions to confront the patients occipital lobes, as illustrated in FIG. 7. In an adult, the first or lowest electrode should be mounted just above the inion, the second electrode should be positioned approximately one hundred millimeters above the first electrode and the third electrode should be behind the ear. The EEG cap 90 includes a band adjustor 91 mounted on the front of a flexible plastic headband such as can be found in chemical face shields or hardhats. The cap includes a 5 cc syringe pump 92 for applying an electrolyte solution through Teflon surgical tubes 93 to the electrodes 100 and scalp after the cap 90 is placed on the head. Various clamps 94 hold the tubes 93, pump 92 and low noise line cable 110 connected to the electrodes 100 in place. Additional details concerning the construction and use of the EEG cap 90 of FIG. 7 can be found in the copending and concurrently filed application entitled Electroencephalographic Cap mentioned in the cross-references to related applications section and which is incorporated herein by reference.

Figure 8:
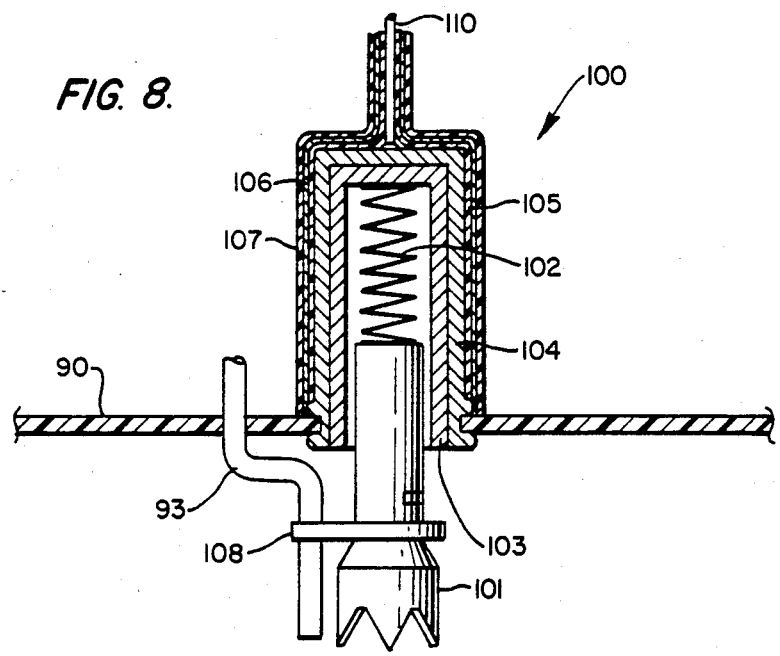
FIG. 8 illustrates the details of the selfpreparing electrodes 100 of FIG. 7.

Each self-preparing electrode 100 includes a tulip probe 101, as illustrated in FIG. 8, which penetrates a keratinous layer of dead skin without penetrating the epidermis beneath and without causing bleeding. The tulip probe 101 is forced through the caratinaceous layer by spring 102 and held in place by probe cartridge 103. The probe cartridge 103 frictionally fits into a probe cartridge holder 104 which snaps into the cap 90. The probe cartridge holder 104 is soldered to the wire cable 110 by electronic solder. Heat shrink tubing 105 surrounds the probe cartridge 104 and is covered by a shield braid 106. The shield braid 106 is connected to a shield of the wiring cable 110, extends down to headband 90 and is surrounded by a second layer of heat shrink tubing 107. The electrolyte is supplied by electrolyte tube 93 which is held in proximity to the tulip probe 101 by tube clamp 108. The tulip probe 101, spring 102 and probe cartridge 103 can be obtained from Ostby-Barton of Warwick, Rhode Island, and are commonly used as probes for electronic circuits. The heat shrink tubing 105 and 107 and the shield braid 106 can be obtained from any electrical supply house. Additional details concerning the construction of self-preparing electrodes can be found in the copending concurrently filed applications mentioned in the crossreferences to related applications section and entitled Subcaratinaceous Electroencephalographic Probe and Shielded Self-preparing Electrode Suitable For Electro-encephalographic Mapping which are both incorporated by reference herein.

Figure 9A:
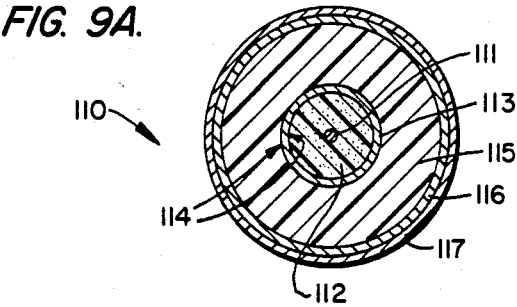
FIGS. 9A and 9B illustrate the construction of the wiring system 110 of the cap in FIG. 7.
Figure 9B:
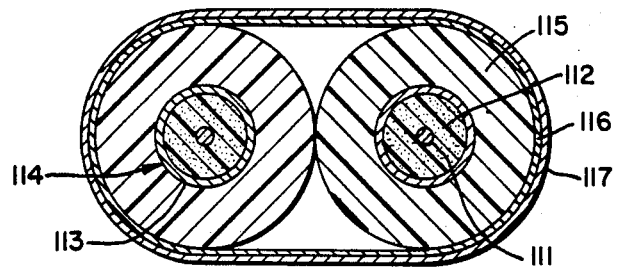

The evoked potentials, produced by the patient 24 and picked up by self-preparing electrodes 100 are conducted over an optimized shielded cable wiring system 110 as depicted in FIGS. 9A and 9B. A conductor 111 is surrounded by polyethylene insulation 112 which is surrounded by a shield layer 113. Between the shield layer 113 and polyethylene insulation 111 is a graphite layer 114 which reduces triboelectric and microphonic-type electrical noise. The shield 113 is surrounded by a Teflon insulation layer 115. A shield braid 116 surrounds the Teflon layer 115 and is covered by heat shrink tubing 117. As can be seen in FIG. 9B, a cable bundle is completely surrounded by the shield braid 116 which extends all the way from amplifier 120 over the electrode 100 completely shielding the signal path from the patient's head to the amplifier 120. The cable interior to the shield braid 116 is a microdot shield cable available from Microtech of Boothwyn, Pennsylvania designated LN1. Of course, the shield braid 116 and heat shrink tubing 117 can be obtained from any electrical supply house. The cap wiring system 110 should be arranged to have as small a loop capture area as possible to reduce unwanted noise. Additional details concerning the construction and use of the low noise wiring system of FIG. 9 can be found in the copending concurrently filed application entitled Low Noise Electroencephalographic Probe Wiring System mentioned in the cross-references to related applications section and which is incorporated herein by reference.

Figure 10:
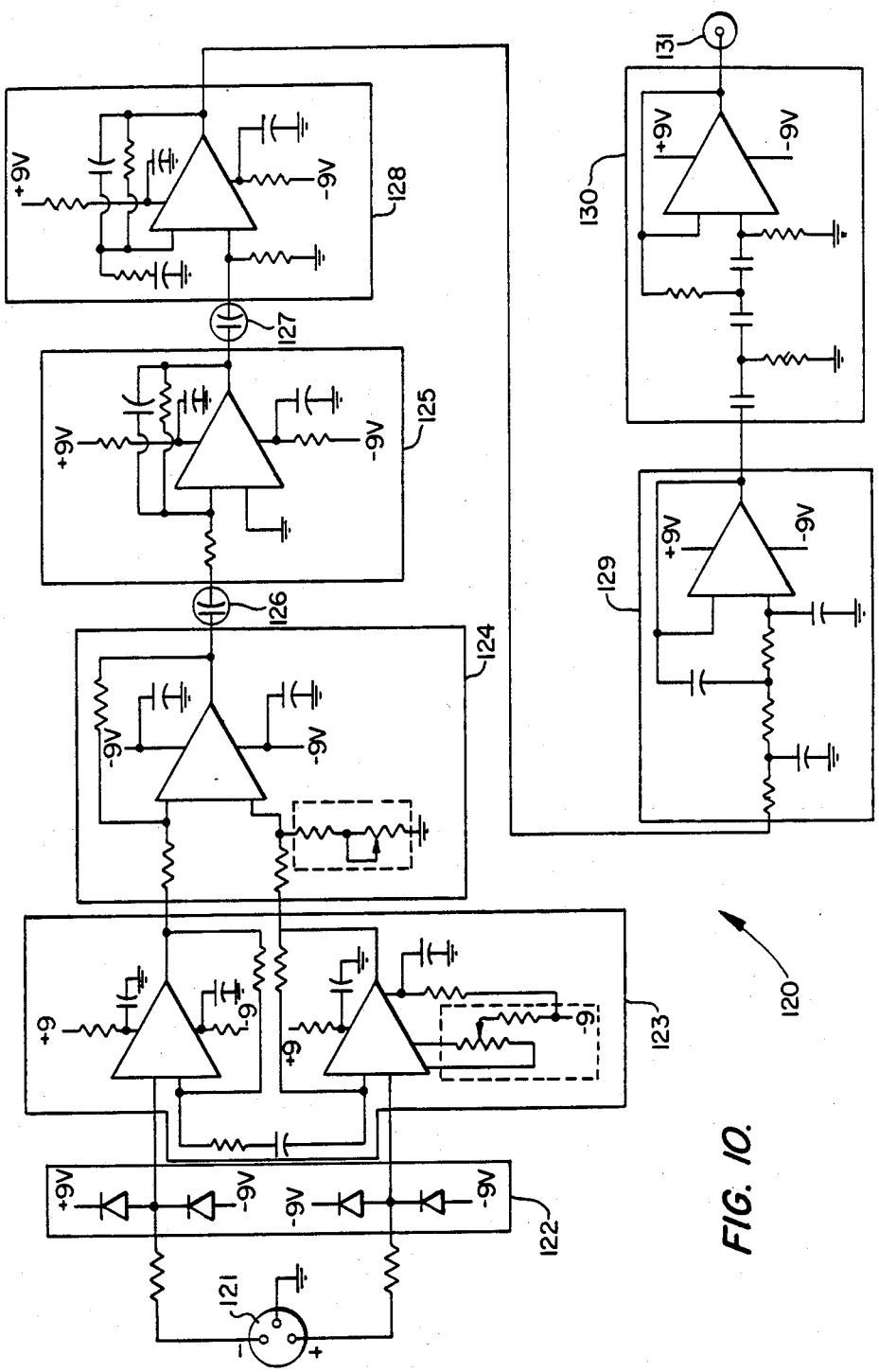
FIG. 10 illustrates the details of the high gain, low noise amplifier 120 of FIG. 2.

The evoked potentials, having a magnitude of 1 to 10 microvolts, are transmitted to a low noise, high gain shielded amplifier 120 having a connector 121, as illustrated in FIG. 10. The connector 121 is connected to a shield case which completely surrounds the amplifier 120. The amplifier 120 is a differential type amplifier providing a gain of approximately $10^6$ and a common mode rejection of 85 dB. The shielded amplifier 120 includes a battery power supply (not shown) inside the shield 120. The evoked potential signals from the subject 24 are applied to a clipping circuit 122 which prevents large amplitude signals from being applied to the amplifying circuits of the amplifier 120. The evoked potential signals are applied to a high impedance element 123 provided to match high impedance electrodes. The input signals are then applied to differential amplifier 124. The differential amplifier is connected to a bandpass filter 125 via an isolating capacitor 126. The bandpass filter 125 transmits the band-limited evoked potential signals through isolating capacitor 127 to a second bandpass filter 128. The second bandpass filter 128 applies the band limited evoked potentials to a lowpass filter 129 which has a bandpass range which overlaps the bandpass range of highpass filter 130. The highly amplified band-limited evoked potential signals exit the shielded amplifier 120 through connector 131. Additional details concerning the construction and operation of the high gain EEG amplifier of FIG. 10 can be found in the copending concurrently filed application entitled Narrow Band Electroencephalographic Amplifier mentioned in the cross-references to related applications section and incorporated by reference herein.

Figure 11:
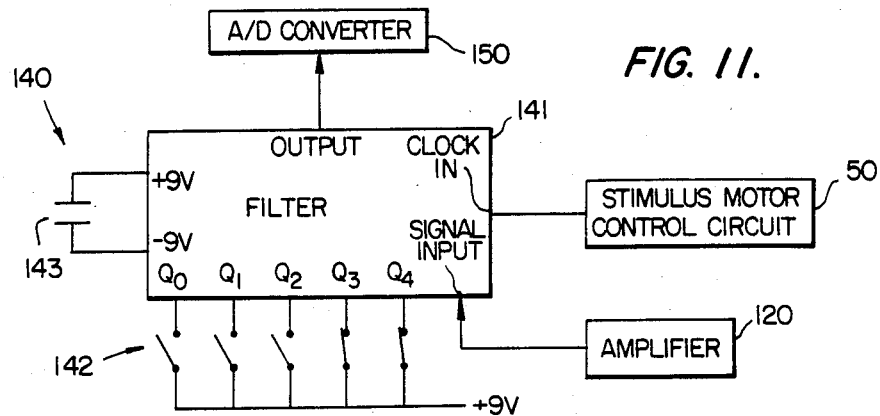
FIG. 11 illustrates the details of the filter 140 of FIG. 2.

The evoked potential signals from amplifier 120 are applied to the filter 140 illustrated in FIG. 11. The filter circuit 141 is a commonly available very narrow bandpass capacitor switched filter in which the bandpass center frequency is controlled by an external 1.2 kilohertz clock signal produced by stimulus motor control circuit 50. The external clock signal is supplied by motor control circuit 50; however, it can be supplied from another source since it does not have to be synchronous with the signals in the control circuit 50. If a 2.4 kilohertz signal is used as the clock signal for filter circuit 141, a 12 hertz center frequency results. The filter circuit 141 can be a hybrid analog/digital filter Model R5620 available from EEG Reticon. The Q inputs of the filter are connected to switches 142 which control the bandwidth of the filter. The switch configuration shown provides a bandpass around six hertz of approximately one hertz when driven by the 1.2 kilohertz clock. A capacitor 143 of 0.01 microfarads is connected across the power supply terminals of the filter chip 141 to suppress power supply noise. The relatively clean six hertz output of the filter chip 141 is applied to the A/D converter 150. The A/D converter samples the six hertz evoked potential output signal produced by the filter 140 every 100 microseconds. As mentioned previously, the analog-to-digital converter is a commercially available unit which also includes a digital input-/output unit 160.

The microcomputer 30 produces a running sum of 255 samples from the analog-to-digital converter 150 which helps remove high frequency converter 150 and filter 140 artifacts and acts as a lowpass filter. That is, as each new sample is produced by analog-to-digital converter 150, the microcomputer 30 subtracts the older sample from the sum and adds the newest sample to the sum thereby providing a running sum of 255 samples. The sum is continuously compared to detect the lowest value or valley in a curve produced by the running sum and the highest value or peak. The peak to peak or peak to valley difference is the amplitude of the evoked potential produced by the patient. This evoked potential amplitude is then lowpass filtered using a 16 point running sum to remove additional noise therein. The 16 point running sum, which is produced every 1/12 seconds, is the average peak to peak amplitude of the evoked potential produced by the patient. The current value of the average peak to peak amplitude is continuously compared to previous peak amplitudes to determine the maximum value. At each new maximum value, the lens position of the continuously variable lens 80 is stored. After each comparison operation, an up or down lens movement pulse is produced by the microcomputer 30 and transmitted to the lens motor control circuit 170 through digital input/output interface 160.

Figure 12:
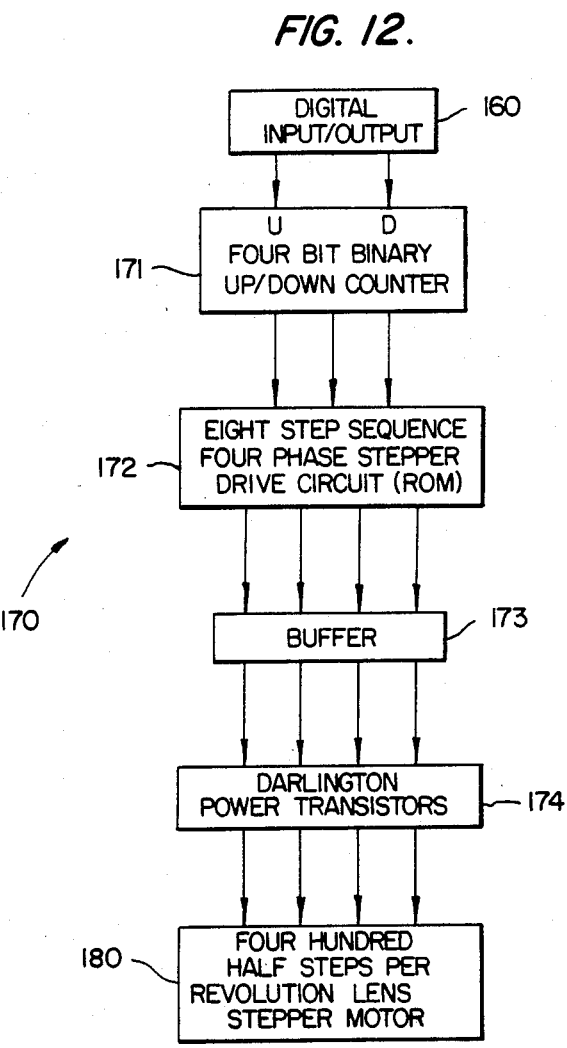
FIG. 12 illustrates the lens stepper motor 180 and control circuit 170 of FIG. 2.

The up and down pulses are applied to the respective inputs of a 4-bit binary up/down counter 171, as illustrated in FIG. 12, which can be a 74LS193 available from Texas Instruments. The output of the up/down counter is applied to an 8-step sequence 4-phase stepper drive circuit which can be a ROM designated DM87S188 manufactured by National Semiconductor. The ROM includes a ROM map as illustrated in Table 1 previously which converts the count in the up/down counter 171 into control signals for lens stepper motor 140. A buffer 173 and Darlington power transistors 174 convert the output of ROM 172 into power signals for the 400 half step per revolution lens stepper motor 180. The buffer 173 can be a CD4050 obtainable from RCA, and the motor 12 can be a Model M03 by SLOSYN of Superior Electric of Bristol, Connecticut and transistors 12 can be MC1411 from Motorola. Additional details concerning the construction and operation of the stepper motor control circuit 170 can be found in the co-pending concurrently filed application entitled Phase Locked Stepper Motor Controlled Light Chopper mentioned in the cross-references to related applications section and which is incorporated by reference herein.

Figure 13A:
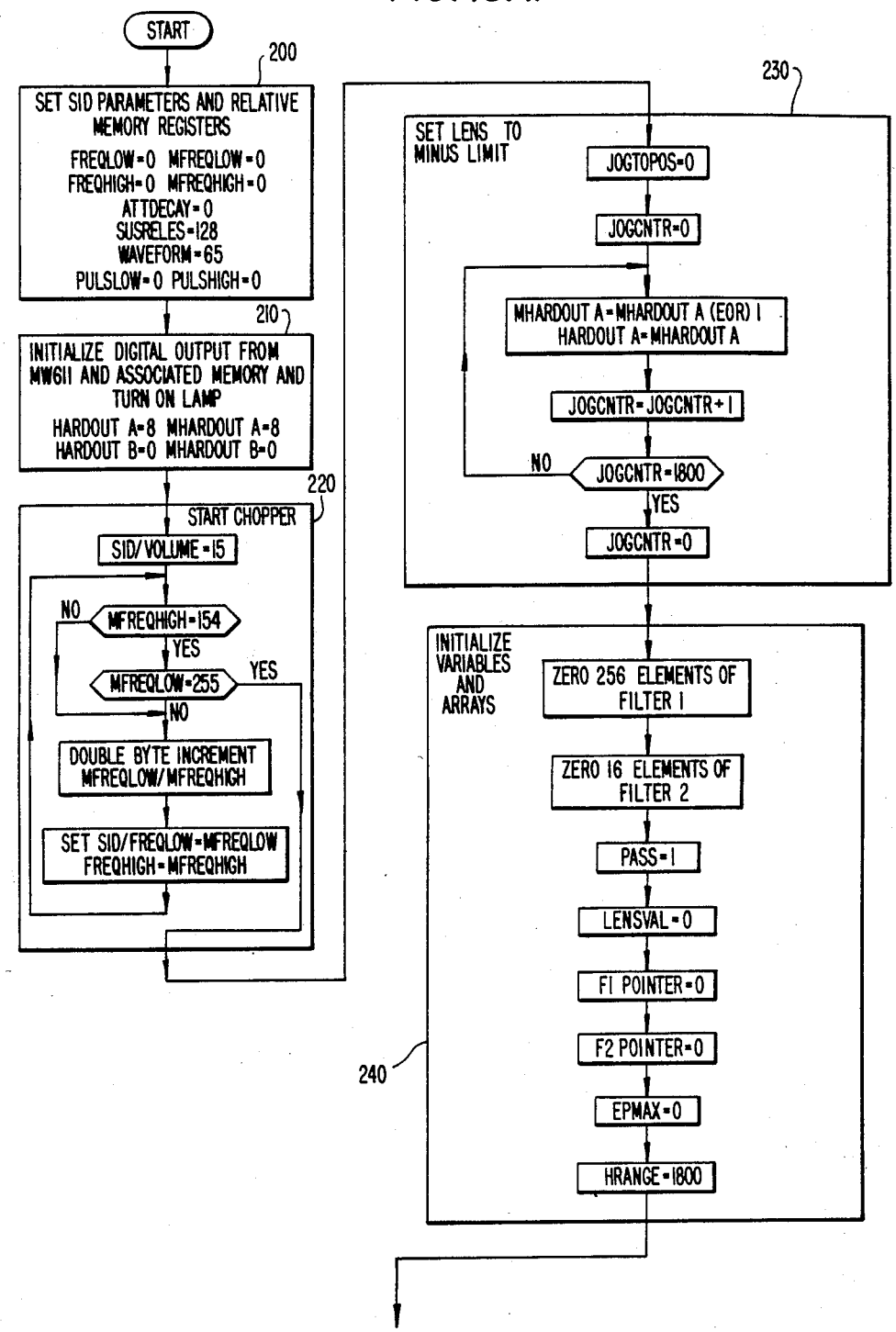
FIGS. 13A-13C illustrate the flowchart for control of the microcomputer 30 of FIG. 2.
Figure 13B:
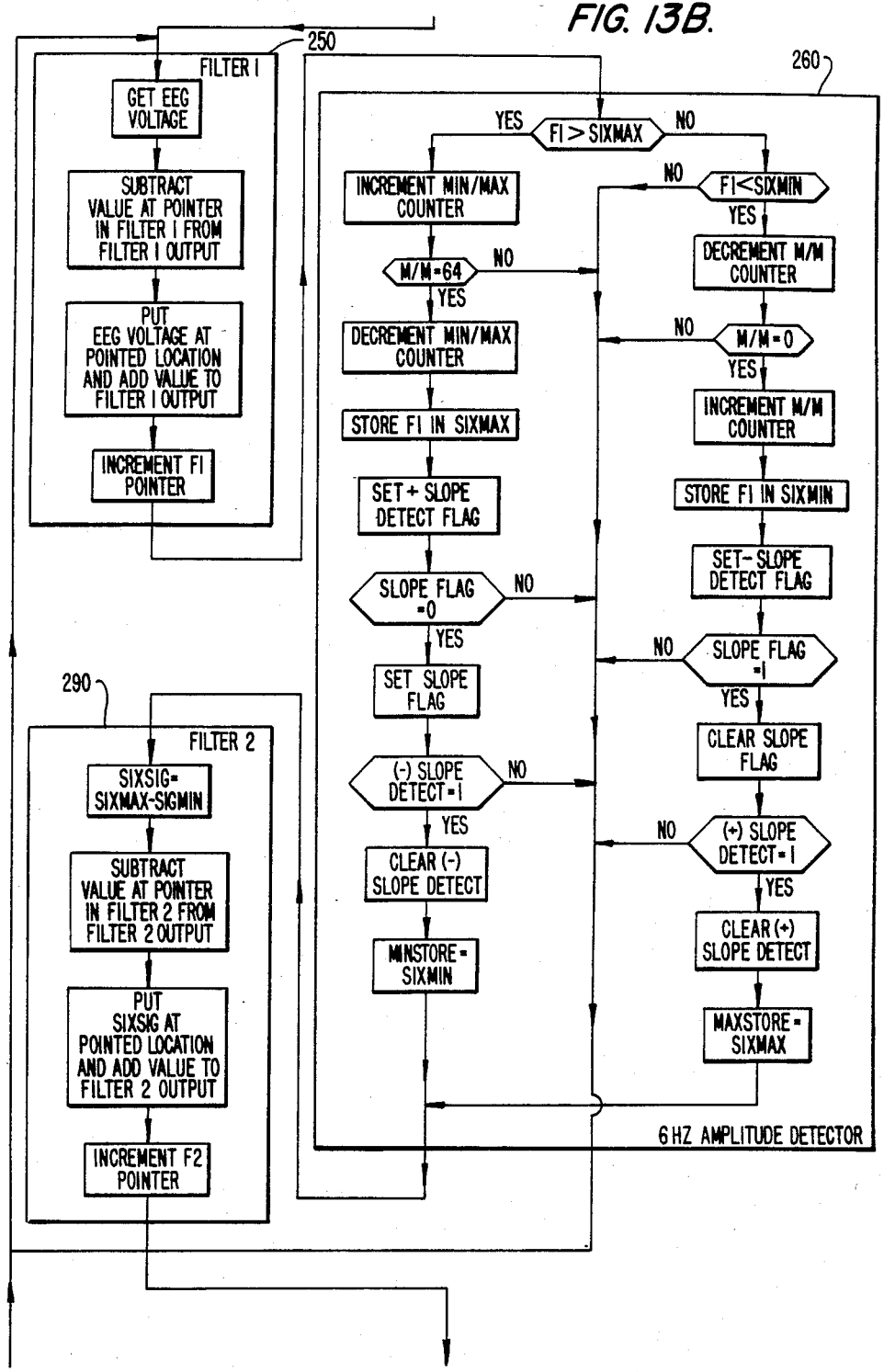
Figure 13C:
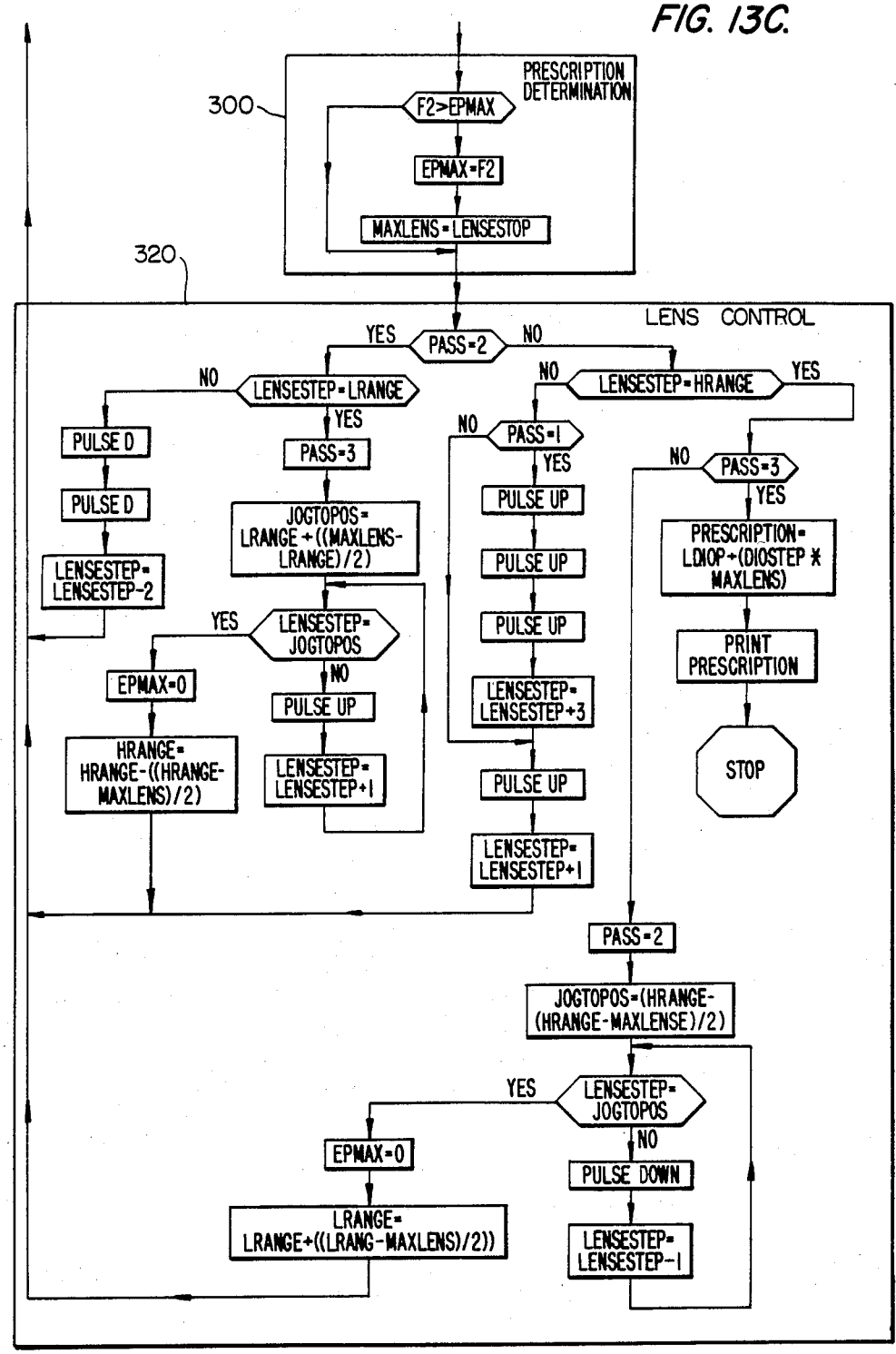

As previously discussed, the microcomputer 30 not only controls the focus of lens 80, but also initiates square wave generator 40 and provides digital filtering of the evoked potentials produced by the patient 24. The operation of the microcomputer is illustrated in detail in the flowcharts of FIGS. 13A–13C. When the system is started, waveform parameters of the system tone generator are set 200. Once the parameters are set, the outputs from the MW611 board are initialized 210. Next, the chopper wheel 71 is started to spin 220 by incrementing until the speed reaches the desired frequency. Next, the lens 80 is set to its minus limit 230 by driving the lens 80 as far as it will go in one direction with the maximum number of steps being 1800. Next, the filter array values are set 240 to appropriate values. A sample from the analog-to-digital converter 150 is obtained and applied 250 to digital filter 1 which produces the 256 point running sum. Next, the resulting sum is applied to a 6 hertz amplitude detector 260 after which the resulting amplitude is applied to the second digital filter 290 which produces the 16 point running sum. Once the amplitude is filtered by the second digital filter 290, the amplitude is compared to the last maximum and the lens 80 position is stored if appropriate. After the prescription is determined 300, lens control 320 is executed in dependence upon the number of the pass of the continuously variable focus lens 80 across the peak amplitude point. In the first pass lens steps are approximately 0.08 diopter, in the second pass lens steps are approximately 0.04 diopter and in the third pass steps are approximately 0.02 diopter. At the end of the third pass, the prescription is printed directly from the lens position if the lens position can be converted directly into diopter measurements or a simple look-up table can be provided in the computer 30 to convert lens position into diopter measurements.

In alternate configurations, the stepper motor control circuit 50 for the stimulus stepper motor 60 could be decoupled from the computer 30. If the stimulus stepper motor control circuit 50 is decoupled, a phase locked stepper motor control circuit such as described in the related application entitled Phase Locked Stepper Motor Controlled Light Chopper could be driven synchronously with a 60 hertz signal available from a wall socket. A different sampling rate for the A/D converter 150 could also be used. Interchangeable colored filters could be provided for light sources 72 and 73 so that color blindness could be tested. A liquid crystal display could also be substituted for the checkerboard mirror stimulus generator as long as a contrast ratio of at least 60 percent is provided. A faster convergence to the patient's prescription can be obtained by allowing the patient to provide a crude subjective focus via adjusting the focus of the telescope 82; however, it would be necessary to communicate the lens 80 position at the crude focus to the lens control program of FIG. 13. In addition, it is also possible to substitute commercially available light gates or shutters for the stepper motor 180 and chopper wheel 171.

The many features and advantages of the invention are apparent from the detailed specification and, thus, it is intended by the appended claims to cover all such features and advantages of the system which fall within the true spirit and scope of the invention. Further, since numerous modifications and changes will readily occur to those skilled in the art, as discussed above, it is not desired to limit the invention to the exact construction and operation illustrated and described, and, accordingly, all suitable modifications and equivalents may be resorted to, falling within the scope of the invention.

We claim:

1. An evoked potential autorefractometry system for a patient, comprising:
   stimulus production means for producing an alternating steady-state stimulus pattern;
   a continuously variable focus lens projecting the stimulus pattern directly to the patient with a continuously changing focus and providing a fixed distance from the pattern to said lens;
   evoked potential sensing means for sensing evoked potentials produced by the patient; and
   control and determination means for determining the maximum amplitude of the evoked potentials, produced by the patient as the focus of the lens is continuously changed, by narrow band asychronous filtering the evoked potentials and detecting amplitude peaks of the evoked potentials.

2. A system as recited in claim 1, wherein the alternating steady-state stimulus pattern comprises an alternating checkerboard alternating at a frequency of approximately six cycles per second.

3. A system as recited in claim 2, wherein said alternating checkerboard has a spacial frequency of 8 cycles per inch at a distance of 32 inches.

4. A system as recited in claim 2, wherein said stimulus production means comprises:
   a pair of light sources;
   a chopper wheel alternately interrupting the light from said pair of light sources; and
   a checkerboard mirror having a reflecting surface reflecting the interrupted light from one of the light sources of said pair toward the patient and transmitting the interrupted light from the other of the light sources of said pair toward said patient.

5. A system as recited in claim 4, wherein said stimulus production means further comprises:
   a first matte filter transmitting the light from one of said pair of light sources;
   a first beam splitter reflecting the light from said first filter toward a reflecting surface of said checkerboard mirror;
   a second matte filter transmitting the light from the other of said pair of light sources; and
   a second beam splitter reflecting the light from the second matte filter through said checkerboard mirror to the patient, the light reflected from and transmitted through the checkerboard mirror passes through said first beam splitter as the light is transmitted to the patient.

6. A system as recited in claim 4, wherein said stimulus production means further comprises:
   a square wave generator;
   a phase locked stepper motor control circuit operatively connected to said square wave generator; and
   a stepper motor connected to said phase locked stepper motor control circuit and said chopper wheel.

7. A system as recited in claim 6, wherein said square wave generator produces a square wave at a frequency of 2.4 filohertz.

8. A system as recited in claim 6, wherein said phase locked stepper motor control circuit comprises:
 a binary counter operatively connected to said square wave generator;
 a read only memory operatively connected to said binary counter; and
 power transistors operatively connected to said read only memory and said stepper motor.

9. A system as recited in claim 4, wherein said chopper wheel is a phase locked stepper motor controlled light chopper.

10. A system as recited in claim 1, wherein said continuously variable focus lens maintains a constant image size as perceived by the patient while continuously changing the focus.

11. A system as recited in claim 1, wherein said continuously variable focus lens comprises:
 a fixed diopter lens receiving the stimulus pattern from said stimulus production means;
 a focusable telescope, coupled to said fixed diopter lens, transmitting the stimulus pattern to the patient; and
 focus means, coupled to said focusable telescope and operatively connected to said control and determination means, for continuously changing the focus of said focusable telescope.

12. A system as recited in claim 11, wherein said fixed diopter lens is a $-1$ diopter close-up lens and said focusable telescope is a $17\times60$ telescope.

13. A system as recited in claim 1, wherein said evoked potential sensing means comprises an electroencephalographic cap.

14. A system as recited in claim 1, wherein said evoked potential sensing means comprises electrodes adapted to be positioned on a head of the patient.

15. A system as recited in claim 1, wherein said evoked potential sensing means comprises:
 an adjustable headband; and
 self-preparing electrodes mounted in said adjustable headband at positions for evoked potential measurement and adapted to penetrate a keratinous layer of skin and contact the epidermis without penetrating same.

16. A system as recited in claim 15, further comprising a shield for and partially surrounding said self-preparing electrodes and connected to ground.

17. A system as recited in claim 15, wherein said evoked potential sensing means further comprises a double shielded wiring system operatively connected to said selfpreparing electrodes and including inner and outer shields and a graphite layer adjacent the inner shield.

18. A system as recited in claim 15, wherein said evoked potential sensing means further comprises a low noise EEG probe wiring system operatively connected to said self-preparing electrodes.

19. A system as recited in claim 15, wherein each of said self-preparing electrodes is a subcaratinaceous EEB probe.

20. A system as recited in claim 15, wherein each of said self-preparing electrodes is a shielded self-preparing electrode suitable for EEB mapping.

21. A system as recited in claim 15, wherein said evoked potential sensing means further comprises electrolyte application means for applying an electrolyte to said self-preparing electrodes and the patient after said self-preparing electrodes are in position.

22. A system as recited in claim 21, wherein said electrolyte application means comprises:
 a pump adapted to pump the electrolyte; and
 tubing, connected to said pump and mounted adjacent to said self-preparing electrode, adapted to convey the electrolyte to said self-preparing electrodes.

23. A system as recited in claim 15, wherein said self-preparing electrodes each comprise:
 a tulip probe; and
 a spring urging said tulip probe through a dead layer of skin without causing bleeding.

24. A system as recited in claim 1, wherein said control and determination means comprises:
 an amplifier, operatively connected to said evoked potential sensing means, receiving the evoked potentials and amplifying same;
 a narrow band noise filter, operatively connected to said amplifier, filtering the evoked potentials to remove environmental noise;
 an analog-to-digital converter, operatively connected to said narrow band noise filter, convering the evoked potentials into digital evoked potentials;
 a computer, operatively connected to said analog-to-digital converter, determining the maximum amplitude of the digital evoked potentials as the focus of the lens is continuously changed, storing the lens position at the maximum amplitude and producing lens control signals; and
 a lens control unit, operatively connected to said computer and said continuously variable focus lens, controlling the focus of said continuously variable focus lens in dependence upon the lens control signals.

25. A system as recited in claim 24, wherein said amplifier comprises a narrow band EEG amplifier.

26. A system as recited in claim 24, wherein said amplifier comprises:
 a clipping circuit operatively connected to said evoked potential sensing means;
 a pair of high impedance low gain amplifying circuits operatively connected to said clipping circuit;
 a differential amplifier operatively connected to said pair of high impedance low gain amplifying circuits;
 a first isolating capacitor operatively connected to said differential amplifier;
 a first bandpass filter operatively connected to said first isolating capacitor;
 a second isolating capacitor operatively connected to said first bandpass filter;
 a second bandpass filter operatively connected to said second isolating capacitor;
 a low pass filter operatively connected to said second bandpass filter;
 a high pass filter operatively connected to said low pass filter and said noise filter; and
 an amplifier shield surrounding said amplifier.

27. A system as recited in claim 24, wherein said noise filter comprises a narrow bandpass filter with a center frequency of six hertz.

28. A system as recited in claim 24,
 wherein said stimulus production means produces a clock signal; and
 wherein said noise filter comprises a narrow band pass filter having a center frequency determined by the clock signal.

29. A system as recited in claim 24, wherein said computer includes:
   means for filtering the evoked potentials using a first running sum;
   means for detecting the peaks of the first running sum;
   means for filtering the peaks using a second running sum; and
   means for determining a maximum of the second running sum and storing the position of the continuously variable focus lens coincident with the maximum of the second running sum.

30. A system as recited in claim 24, wherein said lens control unit comprises:
   a binary up/down counter operatively connected to said computer;
   a read only memory operatively connected to said binary up/down counter;
   power transistors operatively connected to said read only memory; and
   a stepper motor operatively connected to said read only memory and mechanically coupled to said continuously variable focus lens.

31. A system as recited in claim 30, wherein said continuously variable focus lens includes a focus rod member for controlling the focus, and said system further comprises:
   a first sprocket coupled to said focus rod member;
   a second sprocket coupled to said stepper motor; and
   a sprocket chain coupling said first and second sprockets.

32. An evoked potential autorefractometry system for prescribing a lens for a patient, said system comprising:
   a square wave generator generating a square wave of 2.4 kilohertz;
   a stimulus stepper motor and stimulus stepper motor control circuit, operatively connected to said square wave generator, turning said stimulus stepper motor at 3 hertz in dependence upon the square wave;
   a stimulus generator including a checkerboard mirror and a light chopper wheel connected to said stimulus stepper motor, said light chopper wheel causing light to be alternately reflected from the checkerboard mirror toward the patient or transmitted through the checkerboard mirror toward the patient producing an alternating steady state stimulus pattern;
   a continuously variable focus lens projecting the light from the stimulus generator to the patient while maintaining a constant image size and providing a fixed distance from the checkboard mirror to said lens;
   an electoencephalographic cap having selfpreparing electrodes adapted to receive the evoked potentials produced by the patient in response to the light from said stimulus generator;
   a shielded wiring system operatively connected to the self-preparing electrodes of said cap;
   a shielded narrow bandwidth high gain amplifier operatively connected to said shielded wiring system;
   a narrow bandwidth filter, operatively connected to said stepper motor control circuit and said narrow bandwidth high gain amplifier, filtering the evoked potentials;
   a digital-to-analog converter, operatively connected to said narrow bandwidth filter, convering the filtered evoked potentials into digital values;
   a computer, operatively connected to said digital-to-analog converter, asychronously digitally filtering the digital values using a first running sum technique, detecting the amplitude peaks of the first running sum, to digitally filtering the peaks using a second running sum technique, determining the maximum value of the digitally filtered peaks, storing a lens position of said continuously variable focus lens coincident with said maximum and producing lens position control signals; and
   a lens position control circuit and lens stepper motor, operatively connected to said computer and coupled to said continuously variable focus lens, controlling the position of said continuously variable focus lens in dependence upon the lens position control signals.

33. A system as recited in claim 32, wherein said self-preparing electordes are adapted to penetrate a dead layer of skin without causing bleeding.

34. A system as recited in claim 32, wherein the first running sum is produced from 255 points and the second running sum is produced from 16 points.

35. A method for determining visual acuity, comprising:
   a. stimulating a patient with an alternating steadystate stimulus pattern directly through a continuosly focusable constant image size lens;
   b. continuously changing the focus of the lens while maintaining a fixed distance between the lens and the pattern;
   c. detecting evoked potentials produced by the patient;
   d. asychronously filtering the evoked potentials;
   e. detecting the maximum amplitude of the evoked potentials as the focus of the lens is changed; and
   f. storing the lens position of the maximum amplitude.

36. A method as recited in claim 35, wherein step d. includes producing a running sum of evoked potentials.

37. A method as recited in claim 36, wherein step e. includes:
   ei. detecting a peak-to-peak amplitude of the running sum of evoked potentials; and
   eii. producing a running sum of the peak-to-peak amplitude.

38. A continously variable focus lens system receiving a stimulus and transmitting the stimulus to a patient in an evoked potential autorefractometry system, said system comprising:
   a fixed diopter lens receiving the stimulus while maintaining a fixed stimulus to lens distance;
   a focusable telescope, coupled to said fixed diopter lens, transmitting the stimulus to the patient; and
   focus means, coupled to said focusable telescope, for continuously changing the focus of said focusable telescope.

39. A lens system as recited in claim 38, wherein said fixed diopter lens is a +1 diopter close-up lens and said focusable telescope is a 17×60 telescope.

40. A lens system as recited in claim 38, wherein said focus means comprises:
   a stepper motor, mechanically coupled to said telepscope, for changing the focus of said telescope; and
   stepper motor control means for controlling the rotation of said stepper motor.

41. A lens system as recited in claim 40, wherein said stepper motor control means comprises:
pulse means for generating up and down count pulses;
a binary up/down counter operatively connected to said pulse means;
a read only memory operatively connected to said binary up/down counter; and
power transistors operatively connected to said read only memory and said stepper motor.

* * * * *

UNITED STATES PATENT AND TRADEMARK OFFICE
CERTIFICATE OF CORRECTION

PATENT NO. : 4,697,598

DATED : October 6, 1987

INVENTOR(S) : Gary W. Sherwin

Figure 1A:
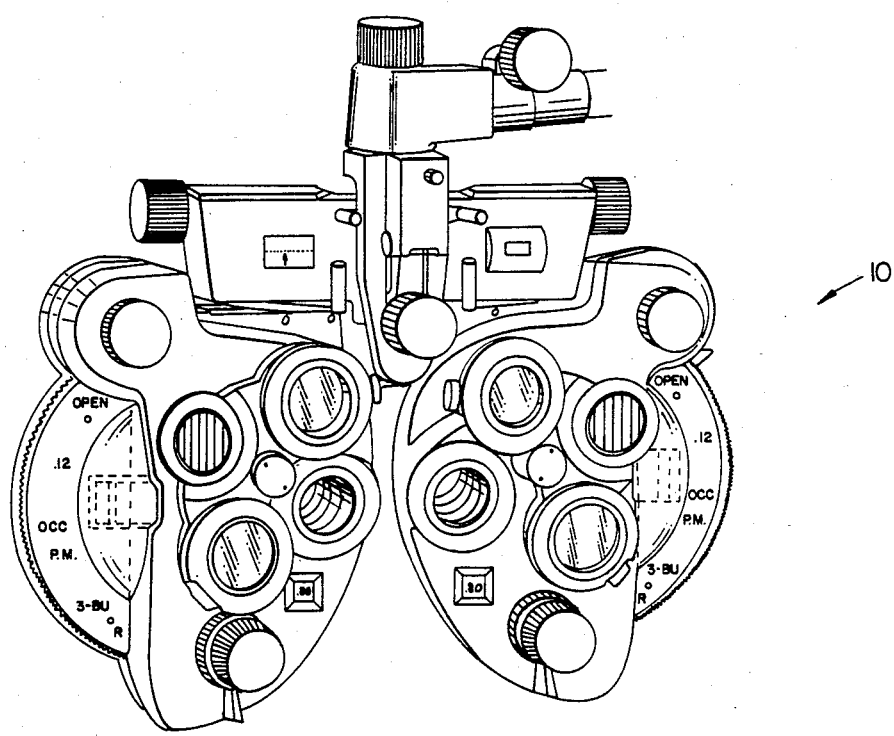
FIG. 1A depicts a prior art refractometer requiring subjective analysis of visual function.
Figure 1B:
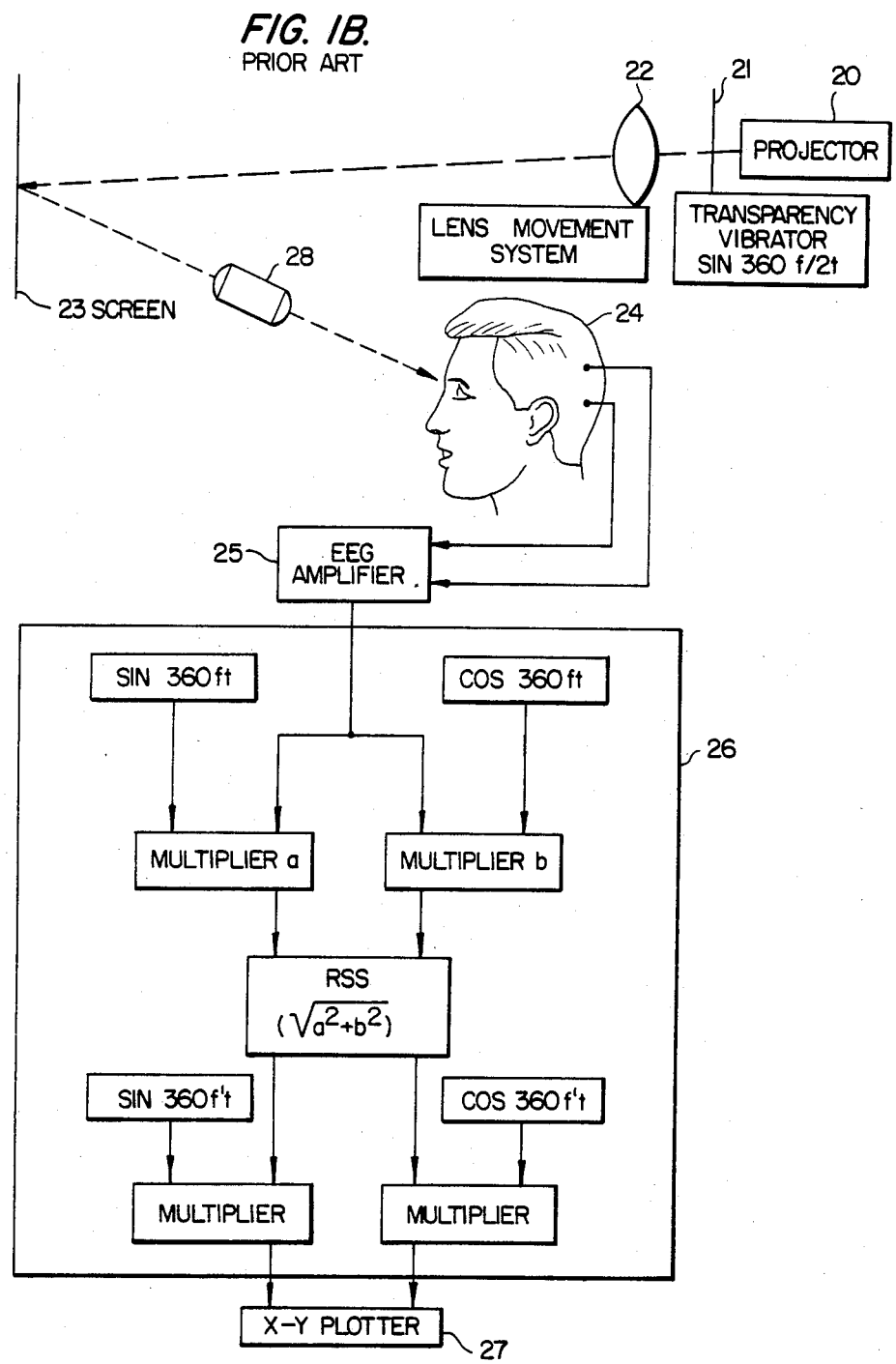
FIG. 1B is a prior art evoked potential acuity analysis system requiring no subjective patient response.

It is certified that error appears in the above-identified patent and that said Letters Patent is hereby corrected as shown below:

Col. 1, line 30, "FIG. 1" should be --FIG. 1A--;

line 37, "nication" should be --nicating verbally with--;

line 67, "used" should be --uses--.

Col. 2, line 67, "acuity" should be --refractometry--;

Col. 3, line 67, "maximum" should be --best--;

line 68, "acuity" should be --focus--.

Col. 5, line 12, "crossreferences" should be --cross references--.

Col. 10, line 30, "spacial" should be --spatial--.

Col. 11, line 51, "selfpreparing" should be --self-preparing--.

Col. 12, line 22, "convering" should be --converting--.

Col. 13, line 56, "selfpreparing" should be --self-preparing--.

UNITED STATES PATENT AND TRADEMARK OFFICE
CERTIFICATE OF CORRECTION

PATENT NO. : 4,697,598

DATED : October 6, 1987

INVENTOR(S) : Gary W. Sherwin

It is certified that error appears in the above-identified patent and that said Letters Patent is hereby corrected as shown below:

Col. 14, line 2, "convering" should be --converting--;

line 8, "filtering" should be --filter--;

line 26, "acuity" should be --refraction--.

Signed and Sealed this

Thirty-first Day of May, 1988

Attest:

DONALD J. QUIGG

*Attesting Officer*  Commissioner of Patents and Trademarks